United States Patent [19]

Hellmuth et al.

[11] 4,025,445

[45] May 24, 1977

[54] BORON AMIDE LUBRICATING OIL ADDITIVE

[75] Inventors: Walter W. Hellmuth, Hopewell Junction; Edward F. Miller, Wappingers Falls, both of N.Y.

[73] Assignee: Texaco Inc., New York, N.Y.

[22] Filed: Dec. 15, 1975

[21] Appl. No.: 640,530

[52] U.S. Cl. .................. 252/49.6; 260/551 B
[51] Int. Cl.$^2$ ............... C10M 1/14; C07F 5/02
[58] Field of Search ............. 260/551 B; 252/49.6

[56] References Cited

UNITED STATES PATENTS

| | | | |
|---|---|---|---|
| 3,000,916 | 9/1961 | Klass et al. | 260/404.5 |
| 3,087,936 | 4/1963 | Le Suer | 252/49.6 X |
| 3,113,106 | 12/1963 | Klass et al. | 44/66 X |
| 3,284,409 | 11/1966 | Dorer | 252/49.6 X |
| 3,284,410 | 11/1966 | Meinhardt | 252/49.6 |
| 3,344,069 | 9/1967 | Steube | 252/49.6 |
| 3,422,016 | 1/1969 | Cyba | 252/49.6 |
| 3,704,308 | 11/1972 | Piasek et al. | 252/49.6 X |

FOREIGN PATENTS OR APPLICATIONS

| | | | |
|---|---|---|---|
| 524,738 | 5/1956 | Canada | 252/49.6 |

*Primary Examiner*—Daniel E. Wyman
*Assistant Examiner*—Thomas A. Waltz
*Attorney, Agent, or Firm*—Thomas H. Whaley; Carl G. Ries; J. J. O'Loughlin

[57] ABSTRACT

A nitrogen-boron-containing lubricant additive characterized by containing from 0.5 to 2.5 weight percent nitrogen and from 0.050 to 2.0 weight percent boron and a mineral lubricating oil composition containing same.

10 Claims, No Drawings

BORON AMIDE LUBRICATING OIL ADDITIVE

BACKGROUND OF THE INVENTION

Field of the Invention

Crankcase motor oil compositions are continuously being reformulated to meet increasingly severe service requirements. Lengthened oil drain intervals in one example of a more severe lubrication requirement. Engine design changes intended to reduce hydrocarbon emissions and exhaust emissions which involve such developments as positive crankcase ventilation and lean burn gasoline engines impose new stresses on the motor oil composition as a result of these engineering advances. At the same time, the anti-rust and anti-sludge forming characteristics of the lubricating oil composition must be maintained under all driving conditions including the relatively severe short trip, cold engine operation.

A further objective of crankcase oil development is to provide a motor oil composition which qualifies as a low-ash lubricant composition and yet maintains its effectiveness for neutralizing acidic blow-by products in the crankcase zone of the engine.

A number of nitrogen-boron-containing additives have been proposed for mineral lubricating oil compositions. The nitrogen-boron-containing lubricant additive of the present development constitutes a novel lubricant additive and it serves to significantly advance the performance of a low-ash lubricant composition as compared to a lubricant with a non-boron containing additive.

SUMMARY OF THE PRIOR ART

U.S. Pat. NO. 3,113,106 discloses a hydrocarbon oil composition containing a rust inhibiting additive obtained by reacting a mixture of polymerized linoleic acids with an alkyl-substituted polyamine at a reaction temperature ranging from 100° to 300° F followed by a reaction with boric acid employing a molar ratio of 0.8 to 2.5 moles of boric acid per mole of said amine.

U.S. Pat. 3,284,410 discloses a lubricating oil composition containing an additive obtained by reacting a hydrocarbon-substituted succinic acid compound having at least 50 aliphatic carbon atoms in the hydrocarbon substituent with at least about 0.5 equivalent of an alkylene amine and at least about 0.1 equivalent of a boron reactant selected from the class containing of boron acids, boron oxide, ammonium salts of boron acids and esters of boron acids with monohydric alcohols.

SUMMARY OF THE INVENTION

The nitrogen-boron-containing lubricating oil additive of the invention is obtained by mixing a chlorinated hydrocarbon having an average molecular weight ranging from about 750 to 2500 containing from about 0.75 to 10 weight percent chlorine with an alkylene polyamine represented by the formula:

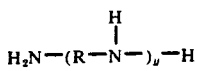

in which R is a divalent ethylene, propylene or polymethylene radical, provided that when R is polymethylene, R represents from 2 to 6 methylene groups and y is an integer from 1 to 10, in the proportion of about 1 to 5 moles of said alkylene polyamine per gram atom of chlorine contained in said chlorinated hydrocarbon and reacting this mixture at a temperature ranging from about 250° to 400° F in the presence of a hydrogen chloride acceptor to form a nitrogen-containing reaction product. This nitrogen-containing reaction product is then combined with a boron compound in the proportion from about 0.20 to 1.5 moles of boron containing compound per mole of said reaction product and the mixture reacted at a temperature in the range from about 200 to 350° F to produce an oil-soluble nitrogen-boron-containing additive characterized by containing from about 0.5 to 2.5 weight percent nitrogen and from about 0.050 to 2.0 weight percent boron. The additive composition of the invention is dissolved in a lubricating oil substrate in an amount effective to produce an anti-rust crankcase lubricating oil composition.

The chlorinated hydrocarbon reactant employed for preparing the novel additive of the invention is any saturated or unsaturated natural or synthetic oil or hydrocarbon which has been chlorinated according to known methods to produce a chlorinated hydrocarbon having an average molecular weight ranging from about 750 to 2500 chlorinated to from about 0.75 to 10 weight percent chlorine. The hydrocarbon radical employed in forming the chlorinated hydrocarbon reactant may be a saturated aliphatic hydrocarbon, such as a highly refined mineral oil or a synthetic alkane which is produced by the hydrogenation of an olefinic polymer. The preferred source of the hydrocarbon radical is an olefin polymer or copolymer obtained from the polymerization of an olefin, such as ethylene, propylene, 1-butene, isobutene, 1-pentene, 1-octene and the like. In general, polymers or copolymers derived from the polymerization of olefins having from 2 to about 8 carbon atoms which following chlorination have an average molecular weight ranging from about 750 to 2500 and contain from about 0.75 to 10 weight percent of chlorine are suitable starting reactants for preparing the additive of the invention. The preferred starting reactant is a polymer of isobutylene having an average molecular weight ranging from about 1000 to 1500 containing from about 2.5 to 7 weight percent of chlorine.

The alkylene polyamine reactant used in the first reaction step for preparing the intermediate reaction product leading to the additive of the invention is represented by the formula:

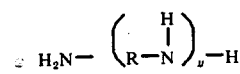

in which R is a divalent ethylene, propylene or polymethylene radical provided that when R is polymethylene, R represents from 2 to 6 methylene groups and y is an integer from 1 to 10. These alkylene polyamine compounds are exemplified by ethylenediamine, diethylenetriamine, triethylenetetra-amine, tetraethylenepentamine, pentaethylenehexamine, trimethylenediamine, tetramethylenediamine, pentamethylenediamine and hexamethylenediamine.

The chlorinated hydrocarbon and the alkylene polyamine are reacted in a proportion ranging from about 1 to 5 moles of alkylene polyamine per gram-atom of chlorine in the chlorinated hydrocarbon. A preferred ratio of reactants for the reaction is from about 1 to 2 moles of alkylene polyamine per gram-atom of chlorine. A hydrogen chloride acceptor is added to the reaction mixture and the reaction is conducted at a temperature ranging from about 250° to 400° F for sufficient time to substantially complete the reaction between the chlorinated hydrocarbon and the alkylene polyamine.

The reaction product obtained from the first reaction is combined with a boron-containing compound and further reacted to produce the nitrogen-boron-containing additive of the invention. The boron compounds which are useful in the second step of the process include boron oxide, boron oxide hydrate, boron triflouride, boron tribromide, boron trichloride, boric acid and other known boron precursor compounds as set forth in U.S. Pat. No. 3,284,410 which disclosure is incorporated herein.

The boron-containing compound is added to the first reaction product in a proportion ranging from about 0.20 to 1.5 moles of said boron compound per mole of said reaction product. This reaction mixture is then heated to a temperature from about 200° to 350° F. and maintained at this temperature for sufficient time to substantially react the boron compound with the first reaction product.

The following examples illustrate the preparation of the nitrogen-containing first reaction product.

EXAMPLE 1

To 105 pounds of chlorinated polyisobutylene having an average molecular weight of about 1250 and containing about 5.3 weight percent chlorine was added 26 pounds of 70% aqueous hexamethylenediamine and 12.6 pounds of 50% aqueous NaOH. The mixture was heated to 400° F and maintained at this temperature for 2 hours. Volatile reaction products were trapped and collected as formed. The reaction mixture was diluted with oil, filtered, and extracted with methanol to remove unreacted hexamethylenediamine. 103 pounds of the reaction product containing 50% diluent oil were recovered having a nitrogen content of 0.71 weight percent.

EXAMPLE 2

To 120 pounds of chlorinated polyisobutylene having an average molecular weight of about 1300 and containing about 2.8 weight percent chlorine was added 21.7 pounds of pentaethylene-hexamine and 5.6 pounds of sodium carbonate. The reaction mixture was heated to about 400° F and maintained at this temperature for about 5 hours. A stream of nitrogen was passed through the reaction mixture to remove the water of reaction. The reaction mixture was diluted with mineral oil (60 pounds) and hydrocarbon solvent (hexane), filtered and extracted with methanol to remove excess pentaethylene-hexamine. 183 pounds of the reaction product was recovered following removal of hexane by stripping at 250° F at reduced pressure. The nitrogen content of the reaction product was 1.3 weight percent.

EXAMPLE 3

3804 grams of chlorinated polyisobutylene having an average molecular weight of about 1300 and containing about 5.6 weight percent chlorine and 618 grams of diethylenetriamine were mixed to give a reaction mixture consisting of about 1.0 moles of diethylene triamine per atom-gram of chlorine. 240 grams of NaOH was added to the reaction mixture and the mixture heated to 374°–392° F and maintained that this temperature for about 5 hours. Volatile reaction products were trapped and removed as formed. The reaction mixture was cooled, diluted with heptane, filtered, and methanol extracted to remove unreacted diethylenetriamine. Heptane solvent was then removed by stripping under reduced pressure at 200° F. The final reaction product was analyzed to contain about 1.8 weight percent nitrogen.

The following examples illustrate the preparation of the nitrogen-boron-containing reaction product of the invention.

EXAMPLE 4

2000 grams of a 50 weight percent oil concentrate of the polyisobutylene-hexamethylene diamine reaction product of Example 1 was heated to 200° F. 27 grams of powdered anhydrous boric acid was added to the heated reaction mixture. The temperature of the reaction mixture was increased to 300° F and maintained at this temperature for 4 hours while collecting the water of reaction overhead. The reaction product was filtered to remove any oil-insoluble reaction products and then analyzed. The final reaction product contained 0.68 weight percent nitrogen and 0.20 weight percent boron.

EXAMPLE 5

2000 grams of a 50 weight percent oil concentrate of the polyisobutylene-hexamethylenediamine reaction product of Example 1 was reacted with 6.8 grams of powdered anhydrous boric acid as in Example 4. The reaction product was found to contain 0.7 weight percent nitrogen and 0.016 weight percent boron.

EXAMPLE 6

2000 grams of a 50 weight percent oil concentrate of the reaction product of Example 1 was reacted with 27 grams of powdered anhydrous boric acid as in Example 4 above. The reaction product was analyzed and found to contain 0.70 weight percent nitrogen and 0.20 weight percent boron.

EXAMPLE 7

2000 grams of a 50 weight percent oil concentrate of the polyisobutylene-hexamethylenediamine reaction product of Example 1 was reacted with 34 grams of powdered anhydrous boric acid as in Example 4 above. The reaction product was analyzed and found to contain 0.64 weight percent nitrogen and 0.26 weight percent boron.

EXAMPLE 8

5000 grams of a 33 weight percent oil concentrate of the polyisobutylene-pentaethylenehexamine reaction product of Example 2 and 115 grams of powdered anhydrous boric acid were reacted as in Example 4 above. The reaction product was analyzed and found to contain 1.3 weight percent nitrogen and 0.41 weight percent boron.

EXAMPLE 9

1000 grams of the polyisobutylene-diethylenetriamine reaction product of Example 3 above was reacted with 27.2 grams of powdered anhydrous boric acid as in Example 4 above. Following reaction, the mixture was diluted with 1000 grams of diluent oil (38.7 SUS at 210° F) and filtered. The reaction product was analyzed and found to contain 0.89 weight percent nitrogen and 0.22 weight percent boron.

EXAMPLE 10

1000 grams of the polyisobutylene-diethylenetriamine reaction product of Example 3 was reacted with 13.6 grams of powdered anhydrous boric acid an in Example 4 above. Following reaction, the mixture was diluted with 1000 grams of diluent oil (38.7 SUS at 210° F) and filtered. The reaction product was analyzed and found to contain 0.90 weight percent nitrogen and 0.11 weight percent boron.

The nitrogen-boron-containing additive of the invention is employed in a mineral lubricating oil composition in order to evaluate its effectiveness. In general, this consists of the mineral oil base and the additive of the invention and conventional lubricating oil additives. The final lubricating oil composition contains from about 85 to 95 weight percent of the mineral lubricating oil substrate.

The base oil employed in the examples below was an essentially paraffinic base oil having an SUS viscosity at 210° F of 40.1.

A Base Blend was prepared from the above-noted base oil and minor amounts of conventional lubricating oil additives to provide viscosity index improvement, anti-oxidant, dispersant and anti-foaming properties. On the basis of a fully formulated lubricating oil composition, the Base Blend contained 0.15 weight percent zinc from zinc di- $C_7$–$C_9$ alkyl dithiophosphate, 0.23 weight percent calcium from calcium carbonate overbased calcium sulfonate with a total base number of 300, 0.50 weight percent of a copolymer of lauryl and stearyl methacrylate, 10 percent of a copolymer of ethylene and propylene having an average molecular weight of about 35,000 and 0.25 weight percent of 2,2'-diethyl-4,4'-t-dioctyldiphenyl-amine.

The nitrogen-boron containing additive of the invention was tested for its effectiveness for reducing bearing weight losses in an internal combustion engine. This was accomplished by adding the additive to the Base Blend described above and testing this lubricating oil composition in the CLR L-38 Engine Test.

The CLR L-38 Oxidation-Corrosion Test is described in Federal Test Method Std. No. 791a, Method 3405. According to this test, the lubricant being tested is employed in a single cylinder Labeco CLR Oil Test Engine equipped with copper-lead connecting rod bearings of known weight. The engine run for 40 hours at 3150 ± 25 RPM. The copperlead bearing are weighed a second time at the end of the test and the bearing weight loss determined.

The test on lubricating oil compositions containing the additive of the invention as well as comparison tests on a lubricating oil composition containing a non-boron nitrogen-containing additive are set forth in the following Table.

TABLE I

| Run | Additive | Additive Analysis Wt. % N | Additive Analysis Wt. % B | Analysis of Blended Lubricant Composition Wt. % N | Analysis of Blended Lubricant Composition Wt. % B | Bearing Weight Loss (mgs.) |
|---|---|---|---|---|---|---|
| 1 | Ex. 1 | 0.71 | — | 0.065 | — | 129.5 |
| 2 | Ex. 1 | 0.71 | — | 0.05 | — | 102.3 |
| 3 | Ex. 4 | 0.68 | 0.20 | 0.05 | 0.15 | 17.0 |
| 4 | Ex. 6 | 0.70 | 0.20 | 0.065 | 0.018 | 40.4 |
| 5 | Ex. 5 | 0.70 | 0.016 | 0.016 | 0.0015 | 64.9 |

TABLE I-continued

| Run | Additive | Additive Analysis Wt. % N | Additive Analysis Wt. % B | Analysis of Blended Lubricant Composition Wt. % N | Analysis of Blended Lubricant Composition Wt. % B | Bearing Weight Loss (mgs.) |
|---|---|---|---|---|---|---|
| 6 | Ex. 7 | 0.64 | 0.26 | 0.065 | 0.026 | 34.9 |
| 7 | Ex. 3 | 1.80 | — | 0.05 | — | 59.1 |
| 8 | Ex. 9 | 0.89 | 0.22 | 0.05 | 0.012 | 26.2 |
| 9 | Ex. 10 | 0.90 | 0.11 | 0.06 | 0.007 | 26.2 |

Runs 3, 4 and 6, 8 and 9 show a dramatic improvement or reduction in the bearing weight loss when the nitrogen-boron-containing additive of the invention is employed in a mineral lubricating oil composition. This substantial improvement makes it possible to provide a lubricant which can pass the CLR L-38 Oxidation-Corrosion Test. Run 5 indicates that there is criticality in the low end of the concentration of the boron in the additive and that this should amount to at least about 0.050 weight percent.

The non-boron-containing additive of Example 2 was compared to the nitrogen-boron-containing additive of Example 8 in the CLR-L-38 Test as in Table I above. The lubricant containing the nitrogen-boron-containing additive reduced the bearing weight loss by 37 percent from that of a lubricant containing the non-boron-containing additive.

The novel nitrogen-boron-containing additive of the invention provides a way of formulating new lubricating oil compositions which exhibit the valuable property of substantially reducing bearing weight losses in an internal combustion gasoline engine.

We claim:

1. An oil-soluble nitrogen and boron-containing lubricant additive prepared by mixing a chlorinated aliphatic hydrocarbon having an average molecular weight ranging from about 750 to 2500 chlorinated to from about 0.75 to 10 weight percent chlorine with an alkylene polyamine, represented by the formula:

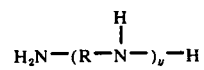

in which R is divalent ethylene, propylene or polymethylene radical, provided that when R is polymethylene, R represents from 2 to 6 methylene groups, and $y$ is an integer from 1 to 10, in the proportion of from about 1 to 5 moles of said alkylene polyamine per gram atom of chlorine contained in said chlorinated hydrocarbon, and reacting said mixture at a temperature in the range from about 250° to 400° F in the presence of a hydrogen chloride acceptor to form a nitrogen-containing reaction product, and reacting said nitrogen-containing reaction product with a boron-containing compound selected from the group consisting of boron oxide, boron oxide hydrate, boron triflouride, boron tribromide, boron trichloride and boric acid, in the proportion of from about 0.20 to 1.5 moles of said boron-containing compound per mole of said nitrogen-containing reaction product at a temperature in the range from about 200 to 350° F to produce a nitrogen-and boron-containing additive characterized by containing from about 0.5 to 2.5 weight percent nitrogen and from about 0.050 to 2.0 weight percent boron.

2. A nitrogen-and boron-containing additive according to Claim 1 in which said chlorinated aliphatic hydrocarbon has an average molecular weight ranging from about 1000 to 1500.

3. A nitrogen-and boron-containing additive according to claim 1 characterized by containing from about 0.8 to 2.0 weight percent nitrogen and from about 0.2 to 0.6 weight percent boron.

4. A nitrogen-and boron-containing additive according to claim 1 in which said chlorinated hydrocarbon reactant is chlorinated polyisobutylene and said alkylene polyamine reactant is hexamethylenediamine.

5. A nitrogen-and boron-containing additive according to claim 1 in which said chlorinated hydrocarbon reactant is chlorinated polyisobutylene having an average molecular weight ranging from about 1000 to 1500 chlorinated to from about 6 to 8 weight percent chlorine and said alkylene polyamine reactant is diethylene triamine.

6. A nitrogen-and boron-containing additive according to Claim 1 in which said boron-containing compound is boric acid.

7. A nitrogen-and boron-containing lubricant additive according to Claim 1 in which the proportion of said boron-containing compound to said reaction product is from about 0.5 to 1.0 moles of said boron-containing compound per mole of said nitrogen-containing product.

8. A lubricating composition comprising a major proportion of a lubricating oil and a minor proportion of the composition of claim 1.

9. A lubricating composition comprising a major proportion of a lubricating oil and a minor proportion of the composition of claim 5.

10. A lubricating composition comprising a major proportion of a lubricating oil and a minor proportion of the composition of claim 7.

\* \* \* \* \*